United States Patent [19]

Böger et al.

[11] 4,418,066
[45] Nov. 29, 1983

[54] PHENYLBENZOYLUREAS

[75] Inventors: Manfred Böger, Weil am Rhein, Fed. Rep. of Germany; Josef Ehrenfreund, Allschwil, Switzerland

[73] Assignee: Ciba-Geigy Corporation, Ardsley, N.Y.

[21] Appl. No.: 263,320

[22] Filed: May 13, 1981

[30] Foreign Application Priority Data

May 14, 1980 [CH] Switzerland .................. 3777/80

[51] Int. Cl.³ .................. A01N 43/40; C07D 213/64
[52] U.S. Cl. ................................ 424/263; 546/291
[58] Field of Search .................. 546/291; 424/263

[56] References Cited

U.S. PATENT DOCUMENTS 4,173,637 11/1979 Nishiyama et al. .................. 546/291
4,173,638 11/1979 Nishiyama et al. .................. 546/291

Primary Examiner—Alan L. Rotman
Attorney, Agent, or Firm—Frederick H. Rabin

[57] ABSTRACT

Novel substituted N-3-(3-chloro-5-trifluoromethyl-2-pyridyloxy)-phenyl-N'-benzoylureas of the formula

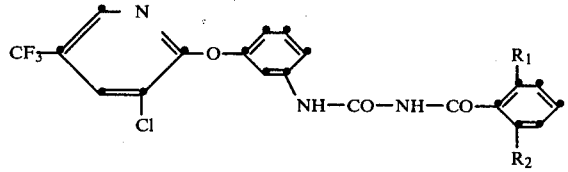

wherein
$R_1$ is fluorine, chlorine, bromine or methyl, and
$R_2$ is hydrogen, fluorine, chlorine or bromine, processes for producing these compounds and compositions containing them for use in combating pests, particularly in combating insects which infest plants and animals. The novel compounds are especially effective against larval stages of insects which damage plants by eating.

10 Claims, No Drawings

PHENYLBENZOYLUREAS

The present invention relates to novel N-3-(3-chloro-5-trifluoromethyl-2-pyridyloxy)-phenyl-N'-benzoylureas, to processes for producing them, and to their use for combating pests. Novel starting materials and their production likewise form subject matter of the invention.

The halogen-substituted N-3-(3-chloro-5-trifluoromethyl-2-pyridyloxy)-phenyl-N'-benzoylureas according to the invention have the formula

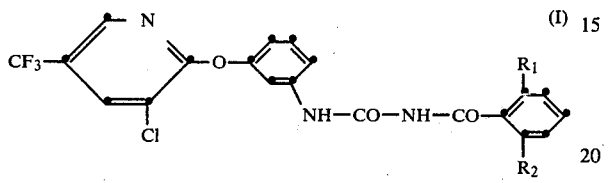

wherein
 $R_1$ is fluorine, chlorine, bromine or methyl, and
 $R_2$ is hydrogen, fluorine, chlorine or bromine.

Preferred compounds of the formula I on account of their activity as pesticidal active substances are those wherein $R_1$ and $R_2$ are fluorine or chlorine. Of special interest are also compounds of the formula I wherein $R_2$ is hydrogen.

The compounds of the formula I can be produced by processes analogous to known processes (cp., inter alia, the German Offenlegungsschriften Nos. 2,123,236 and 2,601,780, and the Japanese Patent Specification No. 5-3103447).

Thus, for example, a compound of the formula I can be produced by reacting (a) the compound of the formula II

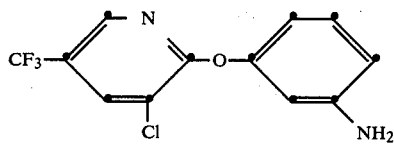

with a compound of the formula III

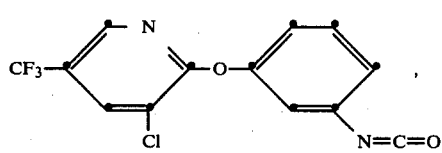

or (b) the compound of the formula IV

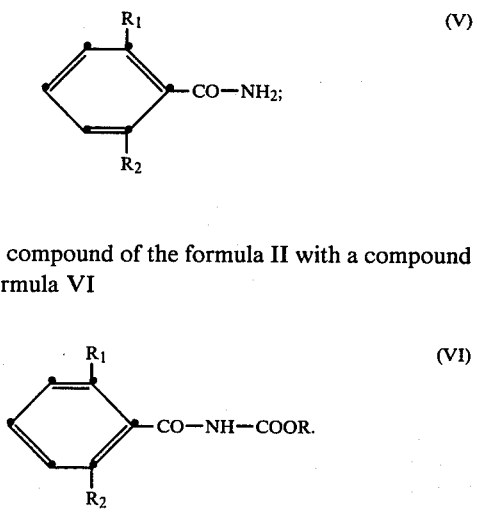

optionally in the presence of an organic or inorganic base, with a compound of the formula V or (c) the compound of the formula II with a compound of the formula VI In the above formulae III, V and VI, the symbols $R_1$ and $R_2$ have the meanings defined under the formula I, and R is a $C_1$–$C_8$-alkyl group, which is unsubstituted or substituted by halogen.

The processes (a), (b) and (c) mentioned are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, particularly benzene, toluene, xylene, chloroform, methylene chloride, carbon tetrachloride and chlorobenzene; nitriles, such as acetonitrile or propionitrile; dimethylsulfoxide, and also ketones, for example acetone, methyl ethyl ketone, methylisopropyl ketone and methylisobutyl ketone. Process (a) is in general performed at a temperature of −10° to 100° C., preferably between 15° and 25° C., optionally in the presence of an organic base, for example triethylamine. Process (b) is performed at a temperature of 0° to 150° C., preferably at the boiling point of the employed solvent, and optionally in the presence of an organic base, such as pyridine, and/or with the addition of an alkali metal or alkaline-earth metal, preferably sodium. For the process (c), that is, for the reaction of the urethane of the formula VI with the aniline of the formula II, the reaction temperature preferred is between about 60° C. and the boiling point of the respective reaction mixture, the solvents used being in particular aromatic hydrocarbons, such as toluene, xylene, chlorobenzene, and so forth.

The starting materials of the formulae III and V are known and can be produced by methods analogous to known methods. The starting materials of the formulae II and IV are however novel compounds, which can be produced by procedures known per se.

The 3-(3-chloro-5-trifluoromethyl-pyridyl-2-oxy)aniline of the formula II can be obtained as follows:

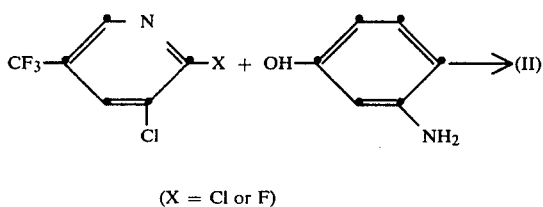

(X = Cl or F)

This reaction is performed at a temperature of 20°–180° C., preferably at 50°–160° C., in the presence of an acid acceptor, for example a hydroxide or hydride of an alkali metal or alkaline-earth metal, preferably KOH or NaOH, as well as of an inert organic solvent, preferably dimethylformamide or dimethylsulfoxide. Furthermore, the aniline of the formula II can be produced, using methods analogous to those described in J. Org. Chem. 29 (1964), 1, by hydrogenation of the corresponding nitro compounds (cp. also the literature cited therein). The aniline of the formula II is obtainable also by chemical reduction (for example by means of Sn-(II)-chloride/HCl) of the corresponding nitro compound (cp. Houben Weyl, "Methoden der org. Chemie" [Methods in organic Chemistry] 11/1, 422).

The benzoylisocyanates of the formula III can be obtained by, inter alia, the following method (cp. J. Agr. Food Chem. 21, 348 and 993; 1973):

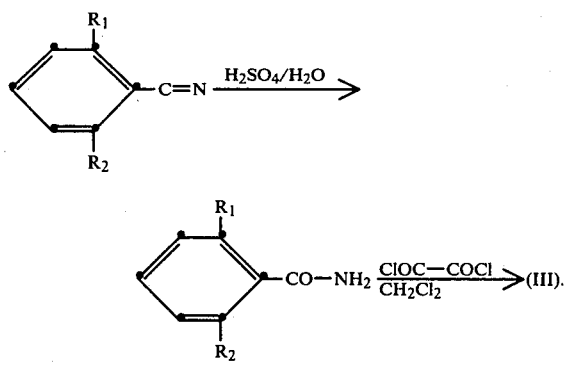

The 3-(3-chloro-5-trifluoromethyl-pyridyl-2-oxy)-phenylisocyanate of the formula IV can be produced for example by reaction of the aniline of the formula II with phosgene using customary processes. The benzamides of the formula V, which are also to be used as starting materials, are known (cp. for example Beilstein "Handbuch der organischen Chemie" [Handbook of organic Chemistry], Vol. 9, p. 336).

The urethanes of the formula VI can be obtained, in a manner known per se, by reaction of a benzoylisocyanate of the formula III with an appropriate alcohol, or by reaction of a benzamide of the formula V, in the presence of a basic compound, with a corresponding ester of chloroformic acid.

It is already known that specific substituted N-phenoxyphenyl-N'-benzoylureas have insecticidal properties. Thus, from the German Offenlegungsschriften Nos. 2,504,982 and 2,537,413 are known halogen-substituted N-4-(2-chloro-4-trifluoromethyl-phenoxy)-phenyl-N'-benzoylureas having insecticidal activity. Also the Japanese Patent Specification No. 5-310447 relates to N-4-(trifluoromethylphenoxy)-phenyl-N'-benzoylureas as insecticidal active substances. Furthermore, in the German Offenlegungsschriften Nos. 2,748,636 and 2,818,830 and also in the Japanese Patent Specification No. 5-4115380 there are described N-4-(2-pyridyloxy)-phenyl-N'-benzoylureas having an insecticidal action.

In contrast to this prior art, compounds of the formula I are novel substituted N-3-(2-pyridyloxy)-phenyl-N'-benzoylureas which surprisingly have increased insecticidal activity, particularly against insects which do damage by eating, such as Spodoptera littoralis and Heliothis virescens. Also the extraordinarily high degree of effectiveness of the compounds of the formula I against eggs and larvae of Musca domestica and Aedas aegypti was not to be anticipated. A further advantage of the compounds of the formula I according to the invention is their very low toxicity to warm-blooded animals and high tolerance to plants.

The compounds of the formula I are especially suitable for combating insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Apart from being used to combat flies, for example Musca domestica, and mosquito larvae, compounds of the formula I can be used also for combating insects which damage plants by eating, in crops of ornamental plants and productive plants, especially in cotton crops (for example against Spodoptera littoralis and Heliothis virescens), and also in fruit and vegetable crops (for example against Laspeyresia pomonella, Leptinotarsa decemlineata and Epilachna varivestis). The compounds of the formula I are distinguished also by a marked action against larval stages of insects, particularly against larval stages of insects which damage plants by eating. When compounds of the formula I are taken up with the feed by insect stages, there occurs in many cases, particularly with regard to Coleoptera, for example Anthonomous grandis, a reduced oviposition and/or a decreased rate of hatching.

The compounds of the formula I can also be used for combating ectoparasites, such as Lucilia sericata, in domestic and productive animals, for example by treatment of animals, livestock housing and pasture land.

The action of the compounds according to the invention or of the compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, carbamates, chlorinates hydrocarbons and bacillus thuringiensis preparations.

The compounds of the formula I can be combined with particular advantage also with substances which have a pesticidally intensifying agent. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and sprays races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations: dusts, scattering agents or granulates (coated granules, impregnated granules and homogeneous granules);

liquid preparations:

(a) water-dispersible concentrates of active substance: wettable powders, pastes and emulsions; and (b) solutions.

The content of active substance in the described compositions is generally between 0.1 and 95%.

The active substances of the formula I can be formulated for example as follows:

Dusts

The following substances are used to produce (a) a 5% dust, and (b) a 2% dust:

(a)
5 parts of active substance,
95 parts of talcum; and (b)
2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with the epoxidised vegetable oil, the mixture is dissolved in 6 parts of acetone, and the polyethylene glycol and cetyl polyglycol ether are then added. The solution obtained is sprayed onto kaolin and the acetone is subsequently evaporated off in vacuo.

Wettable Powders

The following constituents are used to produce (a) a 40% wettable powder, (b) and (c) a 25% wettable powder, and (d) a 10% wettable powder:

(a)
40 parts of active substance,
5 parts of sodium lignin sulfonate,
1 part of sodium dibutyl-naphthalene sulfonate, and
54 parts of silicic acid;

(b)
25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur, and
46 parts of kaolin; and (d)
10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in appropriate mills and rollers to thus obtain wettable powders which can be diluted with water to give suspensions of the concentration required.

Emulsifiable Concentrate

The following substances are used to produce a 10% emulsifiable concentrate:
10 parts of active substance,
3.4 parts of epoxidised vegetable oil,
3.4 parts of a combination emulsifier consisting of fatty alcohol polyglycol ether and alkylaralkylsulfonate calcium salt,
40 parts of dimethylformamide, and
43.2 parts of xylene.

Emulsions of the concentration required can be prepared from a concentrate of this type by dilution with water.

Spray

The following constituents are used to produce a 5% spray:
5 parts of active substance,
1 part of epoxidised vegetable oil, and
94 parts of ligroin (boiling limits 160°–190° C.).

EXAMPLE 1

To 5.8 g of 3-(3-chloro-5-trifluoromethyl-pyridyl-2-oxy)-aniline in 40 ml of anhydrous toluene are added 3.7 g of 2,6-difluorobenzoylisocyanate in 20 ml of anhydrous toluene. After the initial exothermic reaction has subsided, the mixture is allowed to stand overnight. It is then filtered to yield yellow crystals, which are recrystallised from toluene. The product obtained in this manner is N-3-(3-chloro-5-trifluoromethyl-2-pyridyloxy)-phenyl-N'-2,6-difluorobenzoylurea, m.p. 172°–173° C. (compound No. 1).

Production of Starting Compound 50 ml of toluene are added to 12 g of 3-aminophenol, 7.0 g of potassium hydroxide and 100 ml of dimethylsulfoxide, and the mixture is heated to about 150° C. It is left to stand for about 4 hours in order to separate the water. The toluene is subsequently distilled off under normal pressure; the temperature is then lowered to 120° C., and 16.0 g of 2,3-dichloro-5-trifluoromethyl pyridine in 20 ml of dimethyl sulfoxide are added dropwise at this temperature. The reaction mixture is stirred for 8 hours at this temperature; it is afterwards allowed to cool, the pH-value is adjusted to 7 with glacial acetic acid, and the solvents are completely distilled off in vacuo. The residue is taken up in toluene, repeatedly washed with water and dried over sodium sulfate. The oil remaining after removal of the solvent by evaporation is triturated with hexane, whereupon it crystallises. The product thus obtained is 3-(3-chloro-5-trifluoromethyl-pyridyl-2-oxy)-aniline, m.p. 67°–68° C.

The following compounds of the formula I are produced in a manner analogous to that described above:

| Compound No. | $R_1$ | $R_2$ | Melting point (°C.) |
|---|---|---|---|
| 1 | F | F | 172–173 |
| 2 | F | H | 183–184 |
| 3 | Cl | H | 166–169.5 |
| 4 | F | Cl | |
| 5 | Cl | Cl | 183–185 |
| 6 | $CH_3$ | H | |

EXAMPLE 2

Action against *Musca domestica*

50 g of freshly prepared CSMA nutrient medium for maggots were weighed off into each of a series of beakers. A specific amount of a 1% (by weight) acetonic solution of the respective active substance was transferred by pipette to the nutrient medium in each beaker. After a thorough mixing of the nutrient medium, the acetone was allowed to evaporate off for at least 20 hours. There were then deposited per active substance and concentration in each case 25 one-day-old *Musca domestica* maggots into each beaker containing the treated nutrient medium. After completion of pupation, the formed pupae were separated from the nutrient medium by flushing with water, and were placed into vessels closed with perforated lids. The pupae flushed out per batch were counted (toxic effect of the active substance on the development of the maggots), and after 10 days the number of flies which had emerged from the pupae was determined.

Compounds of the formula I according to Example 1 exhibited a good action in the above test.

EXAMPLE 3

Action against *Lucilia sericata*

1 ml of an aqueous solution containing 0.5% of active substance was added to 9 ml of a culture medium at 50° C. About 30 freshly hatched *Lucilia sericata* maggots were then placed onto the culture medium, and after 48 and 96 hours, respectively, the insecticidal action was determined by ascertaining the mortality rate.

Compounds of the formula I according to Example 1 exhibited in this test a good action against *Lucilia sericata*.

EXAMPLE 4

Action against *Aedes aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 two-day-old *Aedes larvae* were placed into each container. The mortality rate was ascertained after 1, 2 and 5 days.

Compounds of the formula I according to Example 1 exhibited in this test a good action against *Aedes aegypti*.

EXAMPLE 5

Insecticidal Stomach-poison Action

Potted cotton plants about 25 cm in height were sprayed with aqueous active-substance emulsions containing the active substance in concentrations of 100, 50, 12.5 and 0.05 ppm. After the drying of the applied coating, larvae of *Spodoptera littoralis* in the $L_3$-stage and of *Heliothis virescens* in the $L_3$-stage, respectively, were settled onto the cotton plants. The test was carried out at 24° C. with 60° relative humidity. The % mortality rate of the test insects was determined after 120 hours.

EXAMPLE 6

Action against *Epilachna varivestis*

*Phaseolus vulgaris* plants (bush beans) about 15–20 cm in height were sprayed with aqueous emulsion preparations containing the respective active substance to be tested, the concentrations being 400 ppm and 800 ppm, respectively. After the drying of the applied coating, 5 larvae of *Epilachna varivestis* (Mexican bean beetle) in the 4th larval stage were settled onto each plant. Over each of the infested plants was placed a plastics cylinder which was closed with a copper-gauze lid. The test was carried out at 28° C. with 60% relative humidity. The acute action (% mortality rate) was determined after 2 and 3 days, respectively. The test insects were observed for a further 3 days to ascertain any damage caused on the plants by eating (antifeeding effect), and also disturbances with respect to development and shedding.

Biological Results

The following Table shows the results of biological tests on compounds according to the invention on the basis of the above biological Examples. The criterion used for ascertaining the results of the tests was the % mortality rate, the applied scale of ratings being as follows:

A: 80–100% mortality rate at a concentration of 0.05 ppm of the active substance tested;
B: 80–100% mortality rate at a concentration of 12.5 ppm of the compound tested;
C: 80–100% mortality rate at a concentration of 50 ppm of the compound tested;
D: 80–100% mortality rate at a concentration of 100 ppm of the compound tested; and
E: 80–100% mortality rate at a concentration of 400 ppm of the compound tested.
F: less than 80% mortality rate at a concentration of 800 ppm of the compound tested.

| | Pesticidal effectiveness | | |
|---|---|---|---|
| Compound No. | *Spodoptera* larvae (Example 5) | *Heliothis* larvae (Example 5) | *Epilachna* larvae (Example 6) |
| 1 | B | A | F |
| 2 | C | D | E |
| 3 | C | C | F |

What is claimed is:
1. A compound of the formula

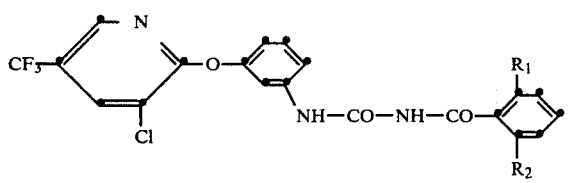

wherein

R₁ is fluorine or chlorine and

R₂ is hydrogen, fluorine or chlorine.

2. A compound according to claim 1, wherein $R_1$ and $R_2$ independently of one another are fluorine or chlorine.

3. A compound according to claim 1, wherein $R_2$ is hydrogen.

4. The compound according to claim 2 of the formula

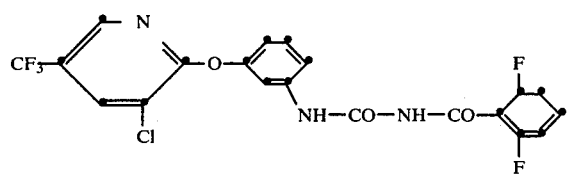

5. The compound according to claim 2 of the formula

6. The compound according to claim 3 of the formula

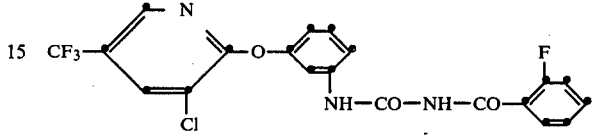

7. The compound according to claim 3 of the formula

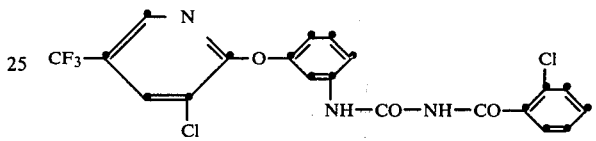

8. A pesticidal composition which comprises a pesticidally effective amount of a compound according to claim 1 in combination with a carrier therefor.

9. A method of combatting pests which comprises applying a pesticidally effective amount of a compound according to claim 1 to said pests or to a locus desired to be protected from said pests.

10. A method according to claim 9 for combating larval stages of insects which damage plants.

* * * * *